United States Patent
Singhal et al.

(10) Patent No.: US 7,242,982 B2
(45) Date of Patent: Jul. 10, 2007

(54) OVERMOLD FOR A MODULAR IMPLANTABLE MEDICAL DEVICE

(75) Inventors: Ruchika Singhal, Minneapolis, MN (US); Darren A. Janzig, Centerville, MN (US); Carl D. Wahlstrand, Lino Lakes, MN (US); Robert M. Skime, Coon Rapids, MN (US); Paulette C. Olson, Eagan, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/730,873

(22) Filed: Dec. 9, 2003

(65) Prior Publication Data

US 2004/0176814 A1    Sep. 9, 2004

Related U.S. Application Data

(60) Provisional application No. 60/507,857, filed on Oct. 1, 2003, provisional application No. 60/503,946, filed on Sep. 20, 2003, provisional application No. 60/503,945, filed on Sep. 20, 2003, provisional application No. 60/471,262, filed on May 16, 2003, provisional application No. 60/431,854, filed on Dec. 9, 2002.

(51) Int. Cl.
    *A61N 1/36* (2006.01)
(52) U.S. Cl. .......................................................... 607/36
(58) Field of Classification Search .................... 607/2, 607/45, 57, 116, 36, 11.11; 623/11.11

See application file for complete search history.

(56) References Cited

U.S. PATENT DOCUMENTS

| | | | |
|---|---|---|---|
| 3,310,051 | A | 3/1967 | Schulte |
| 3,522,811 | A | 8/1970 | Schwartz et al. |
| 3,690,325 | A | 9/1972 | Kenny |
| 3,724,467 | A | 4/1973 | Avery et al. |

(Continued)

FOREIGN PATENT DOCUMENTS

DE          3940632         12/1990

(Continued)

OTHER PUBLICATIONS

U.S. Appl. No. 10/731,868, filed Dec. 9, 2003, entitled "Implantation of Low-Profile Implantable Medical Device."

(Continued)

*Primary Examiner*—Carl Layno
*Assistant Examiner*—Jessica L. Reidel
(74) *Attorney, Agent, or Firm*—Shumaker & Sieffert P.A.

(57) ABSTRACT

A modular implantable medical device permits implantable medical devices to have a smaller profile in order to better fit into locations within the human body. A modular implantable medical device separates various functional components of the implantable medical device into a set of interconnected modules. This distributed architecture of a modular implantable medical device may permit the device footprint to be distributed over a larger area while making the profile smaller, and may permit the overall shape of the implantable medical device to better match the body location into which it is to be implanted. An overmold integrates the modules of a modular implantable medical device into a single structure. In some embodiments the overmold is flexible and provides a biocompatible interface from the component modules and the patient, while restraining potentially harmful intermodule motion.

55 Claims, 12 Drawing Sheets

U.S. PATENT DOCUMENTS

| | | | |
|---|---|---|---|
| 3,913,587 A | 10/1975 | Newash | |
| 4,010,760 A | 3/1977 | Kraska et al. | |
| 4,013,081 A | 3/1977 | Kolenik | |
| 4,040,412 A | 8/1977 | Sato | |
| 4,094,321 A * | 6/1978 | Muto | 607/36 |
| 4,256,115 A | 3/1981 | Bilitch | |
| 4,266,552 A | 5/1981 | Dutcher et al. | |
| 4,328,813 A | 5/1982 | Ray | |
| 4,399,819 A | 8/1983 | Cowdery | |
| 4,399,820 A | 8/1983 | Wirtzfeld et al. | |
| 4,499,907 A | 2/1985 | Kallok et al. | |
| 4,616,655 A | 10/1986 | Weinberg et al. | |
| 4,911,178 A | 3/1990 | Neal | |
| 4,928,696 A | 5/1990 | Henderson et al. | |
| 4,969,899 A | 11/1990 | Cox, Jr. | |
| 4,972,846 A | 11/1990 | Owens et al. | |
| 5,085,644 A | 2/1992 | Watson et al. | |
| 5,197,332 A | 3/1993 | Shennib | |
| 5,220,929 A | 6/1993 | Marquit | |
| 5,271,397 A | 12/1993 | Seligman et al. | |
| 5,314,451 A | 5/1994 | Mulier | |
| 5,314,453 A | 5/1994 | Jeutter | |
| 5,411,538 A | 5/1995 | Lin | |
| H1465 H | 7/1995 | Stokes | |
| 5,455,999 A | 10/1995 | Owens et al. | |
| 5,477,855 A | 12/1995 | Schindler et al. | |
| 5,489,225 A | 2/1996 | Julian | |
| 5,554,194 A | 9/1996 | Sanders | |
| 5,562,715 A | 10/1996 | Czura et al. | |
| 5,571,148 A | 11/1996 | Loeb et al. | |
| 5,573,551 A | 11/1996 | Lin et al. | |
| 5,613,935 A | 3/1997 | Jarvik | |
| 5,638,832 A | 6/1997 | Singer et al. | |
| 5,645,586 A | 7/1997 | Meltzer | |
| 5,674,260 A | 10/1997 | Weinberg | |
| 5,678,559 A | 10/1997 | Drakulic | |
| 5,702,430 A | 12/1997 | Slimon et al. | |
| 5,741,313 A | 4/1998 | Nason et al. | |
| 5,755,743 A * | 5/1998 | Volz et al. | 607/37 |
| 5,769,874 A | 6/1998 | Dahlberg | |
| 5,776,169 A | 7/1998 | Schroeppel | |
| 5,792,067 A | 8/1998 | Karell | |
| 5,800,535 A | 9/1998 | Howard, III | |
| 5,814,095 A | 9/1998 | Müller et al. | |
| 5,836,935 A | 11/1998 | Ashton et al. | |
| 5,843,150 A | 12/1998 | Adams et al. | |
| RE36,120 E | 3/1999 | Karell | |
| 5,895,414 A | 4/1999 | Sanchez-Zambrano | |
| 5,896,647 A | 4/1999 | Shkuratoff | |
| 5,919,215 A | 7/1999 | Haeg et al. | |
| 5,935,154 A | 8/1999 | Westlund | |
| 5,941,905 A | 8/1999 | Single | |
| 5,941,906 A | 8/1999 | Barreras, Sr. et al. | |
| 5,954,757 A | 9/1999 | Gray | |
| 5,984,859 A | 11/1999 | Lesinski | |
| 5,991,664 A | 11/1999 | Seligman | |
| 6,006,124 A | 12/1999 | Fischell et al. | |
| 6,016,449 A | 1/2000 | Fischell et al. | |
| 6,061,593 A | 5/2000 | Fischell et al. | |
| 6,067,474 A | 5/2000 | Schulman et al. | |
| 6,091,979 A | 7/2000 | Madsen | |
| 6,128,538 A | 10/2000 | Fischell et al. | |
| 6,131,581 A | 10/2000 | Leysieffer et al. | |
| 6,134,474 A | 10/2000 | Fischell et al. | |
| 6,154,677 A | 11/2000 | Leysieffer | |
| 6,168,580 B1 | 1/2001 | Yardley | |
| 6,176,879 B1 | 1/2001 | Reischl et al. | |
| 6,214,032 B1 | 4/2001 | Loeb et al. | |
| 6,230,049 B1 | 5/2001 | Fischell et al. | |
| 6,248,080 B1 | 6/2001 | Miesel et al. | |
| 6,248,126 B1 | 6/2001 | Lesser et al. | |
| 6,259,951 B1 | 7/2001 | Kuzma et al. | |
| 6,266,556 B1 | 7/2001 | Ives et al. | |
| 6,269,266 B1 | 7/2001 | Leysieffer | |
| 6,272,382 B1 | 8/2001 | Faltys et al. | |
| 6,308,101 B1 | 10/2001 | Faltys et al. | |
| 6,324,428 B1 | 11/2001 | Weinberg et al. | |
| 6,324,433 B1 | 11/2001 | Errico | |
| 6,330,468 B1 | 12/2001 | Scharf | |
| 6,354,299 B1 | 3/2002 | Fischell et al. | |
| 6,356,792 B1 | 3/2002 | Zonenshayn et al. | |
| 6,358,281 B1 | 3/2002 | Berrang et al. | |
| 6,360,122 B1 | 3/2002 | Fischell et al. | |
| 6,366,813 B1 | 4/2002 | DiLorenzo | |
| 6,415,184 B1 | 7/2002 | Ishikawa et al. | |
| 6,427,086 B1 | 7/2002 | Fischell et al. | |
| 6,445,956 B1 | 9/2002 | Laird et al. | |
| 6,480,743 B1 | 11/2002 | Kirkpatrick et al. | |
| 6,490,486 B1 | 12/2002 | Bradley | |
| 6,505,077 B1 | 1/2003 | Kast et al. | |
| 6,516,227 B1 | 2/2003 | Meadows et al. | |
| 6,516,808 B2 | 2/2003 | Schulman | |
| 6,537,200 B2 | 3/2003 | Leysieffer et al. | |
| 6,554,762 B2 | 4/2003 | Leysieffer | |
| 6,560,486 B1 | 5/2003 | Osorio et al. | |
| 6,565,503 B2 | 5/2003 | Leysieffer et al. | |
| 6,567,703 B1 | 5/2003 | Thompson et al. | |
| 6,575,894 B2 | 6/2003 | Leysieffer et al. | |
| 6,597,954 B1 | 7/2003 | Pless et al. | |
| 6,618,623 B1 * | 9/2003 | Pless et al. | 607/45 |
| 6,626,680 B2 | 9/2003 | Ciurzynski et al. | |
| 6,648,914 B2 | 11/2003 | Berrang et al. | |
| 6,671,544 B2 | 12/2003 | Baudino | |
| 6,726,678 B1 | 4/2004 | Nelson et al. | |
| 6,736,770 B2 | 5/2004 | Leysieffer et al. | |
| 6,788,974 B2 * | 9/2004 | Bardy et al. | 607/36 |
| 6,805,998 B2 | 10/2004 | Jenson et al. | |
| 6,977,124 B2 * | 12/2005 | Probst et al. | 429/163 |
| 7,103,415 B2 * | 9/2006 | Probst et al. | 607/36 |
| 2001/0033953 A1 | 10/2001 | Takeuchi et al. | |
| 2001/0051819 A1 | 12/2001 | Fischell et al. | |
| 2002/0002390 A1 | 1/2002 | Fischell et al. | |
| 2002/0013612 A1 | 1/2002 | Whitehurst | |
| 2002/0019669 A1 | 2/2002 | Berrang et al. | |
| 2002/0051550 A1 | 5/2002 | Leysieffer | |
| 2002/0068958 A1 | 6/2002 | Bardy et al. | |
| 2002/0072770 A1 | 6/2002 | Pless | |
| 2002/0077670 A1 | 6/2002 | Archer et al. | |
| 2002/0099412 A1 | 7/2002 | Fischell et al. | |
| 2002/0103510 A1 | 8/2002 | Bardy et al. | |
| 2002/0161403 A1 | 10/2002 | Meadows et al. | |
| 2002/0165588 A1 | 11/2002 | Fraley et al. | |
| 2002/0169485 A1 | 11/2002 | Pless et al. | |
| 2002/0177882 A1 | 11/2002 | DiLorenzo | |
| 2003/0004428 A1 | 1/2003 | Pless et al. | |
| 2003/0004546 A1 | 1/2003 | Casey | |
| 2003/0040781 A1 | 2/2003 | Sunderland et al. | |
| 2003/0073972 A1 * | 4/2003 | Rosenman et al. | 604/502 |
| 2003/0085684 A1 | 5/2003 | Tsukamoto et al. | |
| 2003/0088294 A1 | 5/2003 | Gesotti | |
| 2003/0109903 A1 | 6/2003 | Berrang et al. | |
| 2003/0130706 A1 | 7/2003 | Sheffield et al. | |
| 2003/0171787 A1 | 9/2003 | Money et al. | |
| 2004/0082977 A1 | 4/2004 | Engmark et al. | |
| 2004/0173221 A1 * | 9/2004 | Singhal et al. | 128/898 |
| 2004/0176750 A1 | 9/2004 | Nelson et al. | |
| 2004/0176819 A1 * | 9/2004 | Wahlstrand et al. | 607/45 |
| 2005/0004620 A1 * | 1/2005 | Singhal et al. | 607/45 |
| 2005/0004637 A1 * | 1/2005 | Singhal et al. | 607/116 |

FOREIGN PATENT DOCUMENTS

| | | |
|---|---|---|
| EP | 1 145 735 A2 | 10/2001 |
| EP | 1 145 736 A2 | 10/2001 |

| | | |
|---|---|---|
| GB | 1 161 579 | 8/1969 |
| WO | WO 92/20402 | 11/1992 |
| WO | WO 99/06108 | 2/1999 |
| WO | WO 99/34758 | 7/1999 |
| WO | WO 00/13743 | 3/2000 |
| WO | WO 00/40295 | 7/2000 |
| WO | WO 01/10369 | 2/2001 |
| WO | WO 01/28622 | 4/2001 |
| WO | WO 01/39830 | 6/2001 |
| WO | WO 01/41858 | 6/2001 |
| WO | WO 01/60450 | 8/2001 |
| WO | WO 01/97906 | 12/2001 |
| WO | WO 02/05590 | 1/2002 |
| WO | WO 02/056637 | 7/2002 |
| WO | WO 02/083207 | 10/2002 |
| WO | WO 02/083208 | 10/2002 |
| WO | WO 02/083233 | 10/2002 |
| WO | WO 03/026739 | 4/2003 |
| WO | WO 03/076012 | 9/2003 |
| WO | WO 2004/043536 | 5/2004 |
| WO | WO 2004/052458 | 6/2004 |

OTHER PUBLICATIONS

U.S. Appl. No. 10/731,699, filed Dec. 9, 2003, entitled "Coupling Module of a Modular Implantable Medical Device."
U.S. Appl. No. 10/731,881, filed Dec. 9, 2003, entitled "Reducing Relative Intermodule Motion in a Modular Implantable Medical Device."
U.S. Appl. No. 10/730,878, filed Dec. 9, 2003, entitled "Lead Interconnect Module of a Modular Implantable Medical Device."
U.S. Appl. No. 10/730,877, filed Dec. 9, 2003, entitled "Low-Profile Implantable Medical Device."
U.S. Appl. No. 10/731,867, filed Dec. 9, 2003, entitled "Concavity of an Implantable Medical Device."
U.S. Appl. No. 10/731,638, filed Dec. 9, 2003, entitled "Modular Implantable Medical Device."
U.S. Appl. No. 10/731,869, filed Dec. 9, 2003, entitled "Modular Implantable Medical Device."
"Surgical Process," Animation Screenshots from http://www.cochlearamerica.com/800.asp, 7 pgs.
"Candidate Brochure," http://www.cochlearamerica.com/pdfs/candidatebrochglobal.pdf, 14 pgs.
"Research and Development," http://www.cochlearamericas.com/384.asp, 1 pg.
"The World Leader in cochlear implants—revolutionizing hearing for adults and infants," http://www.cochlear.com, 1 pg.
"Cochlear: innovator of the Nucleus 3 cochlear implant system," http://www.cochlearamericas.com, 1 pg.
"What is a Cochlear Implant," http://www.cochlearamericas.com/What/161.asp, 1 pg.
"ESPrit 3G Speech Processor," http://www.cochlearamericas.com/591.asp, 2 pgs.
"Nucleus 3 System," http://www.cochlearamericas.com/Products/465.asp, 1 pg.
"Internal Components: Nucleus 24 Cochlear Implants," http://www.cochlearamericas.com/374.asp, 1 pg.
"Nucleus 24 Contour," http://www.cochlearamericas.com/568.asp, 2 pgs.
"Nucleus 24 M," http://www.cochlearamericas.com/372.asp, 1 pg.
"Nucleus 24 K," http://www.cochlearamericas.com/371.asp, 1 pg.
"Nucleus 24 Double Array," http://www.cochlearamericas.com/370.asp, 1 pg.
"Nucleus 24 ABI: Auditory Brainstem Implant," http://www.cochlearamericas.com/373.asp, 2 pgs.
"Nucleus Speech Processors," http://www.cochlearamericas.com/629.asp, 1 pg.
"Sprint: body worn speech processor," http://www.cochlearamericas.com/1010.asp, 1 pg.
"Cochlear," http://www.cochlearamericas.com/Recipients/978.asp, 3 pgs.
Notification of Transmittal of the International Search Report dated May 7, 2004, International Application No. PCT/US03/38928.
Written Opinion dated Dec. 16, 2004, International Application No. PCT/US03/38928.
Notification of Transmittal of the International Preliminary Examination Report dated Apr. 11, 2005, International Application No. PCT/US03/38928.
U.S. Appl. No. 10/835,527, filed Apr. 29, 2004, entitled "Implantation of Implantable Medical Device."
U.S. Appl. No. 10/835,232, filed Apr. 29, 2004, entitled "Explantation Of Implantable Medical Device."
U.S. Appl. No. 10/835,233, filed Apr. 29, 2004, entitled "Implantable Medical Device With A Nonhermetic Battery."
U.S. Appl. No. 10/835,548, filed Apr. 29, 2004, entitled "Headset Recharger For Cranially Implantable Medical Devices."
U.S. Appl. No. 10/835,245, filed Apr. 29, 2004, entitled "Battery Housing Configuration."
U.S. Appl. No. 10/837,276, filed Apr. 30, 2004, entitled "Implantable Medical Device With Anti-Infection Agent."
Notification of the International Preliminary Report on Patentability for International Application No. PCT/US2004/022109, filed Jul. 12, 2004, 11 pgs. (Sep. 6, 2005).

* cited by examiner

OVERMOLD FOR A MODULAR IMPLANTABLE MEDICAL DEVICE

This application claims priority from:
1. U.S. Provisional Application Ser. no. entitled "CRANIAL NEUROSTIMULATOR AND METHOD," Ser. No. 60/431,854, filed on Dec. 9, 2002;
2. U.S. Provisional Application entitled "IMPLANTABLE CRANIAL MEDICAL DEVICES AND METHODS," Ser. No. 60/471,262, filed on May 16, 2003;
3. U.S. Provisional Application entitled "IMPLANTABLE CRANIAL MEDICAL DEVICES AND METHODS," Ser. No. 60/503,945, filed on Sep. 20, 2003;
4. U.S. Provisional Application entitled "IMPLANTABLE CRANIAL MEDICAL DEVICES AND METHODS," Ser. No. 60/503,946, filed on Sep. 20, 2003; and
5. U.S. Provisional Application entitled "THIN NEURO STIMULATION SYSTEM, DEVICE AND METHOD," Ser. No. 60/507,857, filed on Oct. 1, 2003. The entire content of each of these U.S. Provisional Applications is incorporated herein by reference.

The following co-pending and commonly-assigned U.S. Patent Applications, filed on even date herewith, are also incorporated herein by reference:
1. U.S. patent application Ser. No. 10/731,869, entitled "MODULAR IMPLANTABLE MEDICAL DEVICE," to Wahlstrand et al., filed Dec. 9, 2003;
2. U.S. patent application Ser. No. 10/731,868, entitled "IMPLANTATION OF LOW-PROFILE IMPLANTABLE MEDICAL DEVICE," to Singhal et al., filed Dec. 9, 2003;
3. U.S. patent application Ser. No. 10/731,881, entitled "REDUCING RELATIVE INTERMODULE MOTION IN A MODULAR IMPLANTABLE MEDICAL DEVICE," to Wahlstrand et al., filed Dec. 9, 2003;
4. U.S. patent application Ser. No. 10/731,699, entitled "COUPLING MODULES OF A MODULAR IMPLANTABLE MEDICAL DEVICE," to Janzig et al., filed Dec. 9, 2003;
5. U.S. patent application Ser. No. 10/731,877, entitled "LOW-PROFILE IMPLANTABLE MEDICAL DEVICE," to Janzig et al., filed Dec. 9, 2003;
6. U.S. patent application Ser. No. 10/731,867, entitled "CONCAVITY OF AN IMPLANTABLE MEDICAL DEVICE," to Wahlstrand et al., filed Dec. 9, 2003;
7. U.S. patent application Ser. No. 10/730,878, entitled "LEAD CONNECTION MODULE OF A MODULAR IMPLANTABLE MEDICAL DEVICE," to Singhal et al., filed Dec. 9, 2003; and
8. U.S. patent application Ser. No. 10/731,638, entitled "MODULAR IMPLANTABLE MEDICAL DEVICE," to Wahlstrand et al., filed Dec. 9, 2003.

TECHNICAL FIELD

The invention relates to medical devices, and more particularly, to implantable medical devices that deliver therapy to and/or monitor a patient.

BACKGROUND

Depending on the application for which they are implanted in a patient, implantable medical devices (IMDs) may include a variety of electrical and/or mechanical components. Typically, an IMD includes a rigid housing that houses all of its components, which are generally fragile, to protect the components from forces to which they would otherwise be exposed when implanted within the human body. In order to avoid potentially harmful interactions between the components and bodily fluids, e.g., corrosion, IMD housings are typically hermetically sealed. Many IMD housings are fabricated from Titanium because of its desirable rigidity and biocompatibility.

The size and shape of an IMD housing is dependant on the sizes and shapes of the components of the IMD. Large components common to most IMDs include a battery, a telemetry coil, and a hybrid circuit that includes digital circuits, e.g., integrated circuit chips and/or a microprocessor, and analog circuit components. Attempts have been made to reduce the size of the IMD housing by reducing the size of these components, changing the shape of these components, and organizing these components within the IMD housing to avoid empty space within the housing. Despite these efforts to reduce the size of IMD housings, the size, shape and rigidity of IMD housings still greatly limits the locations within the human body where an IMD can be practically implanted.

Due to these limitations, an IMD is typically implanted within the abdomen, upper pectoral region, or subclavicular region of a patient. Leads or catheters must be used in order to deliver therapy or monitor a physiological parameter at a location of the body other than where the IMD is implanted. Implantation and positioning of leads and catheters can be difficult and time-consuming from the perspective of a surgeon, particularly where the IMD is located a significant distance from the treatment or monitoring site. Moreover, the increased surgical time, increased surgical trauma, and increased amount of implanted material associated with the use of leads and catheters can increase the risk to the patient of complications associated with the implantation of an IMD.

For example, IMDs that are used to treat or monitor the brain, e.g., to deliver deep brain stimulation (DBS) therapy, are implanted some distance away from the brain, e.g., within the subclavicular region of patients. The long leads that connect the implantable medical device to electrodes implanted within the brain require tunneling under the scalp and the skin of the neck, thereby requiring increased surgery and a prolonged amount of time under general anesthesia during the implant procedure. In some cases, tunneling the leads under the scalp and skin of the neck requires an additional surgical procedure under general anesthesia. The lengthy tract along the leads is more susceptible to infection, and the leads can erode the overlying scalp, forcing removal so that the scalp can heal. Further, the long leads running under the scalp and through the neck are more susceptible to fracture due to torsional and other forces caused by normal head and neck movements.

SUMMARY

In general, the invention relates to an overmold for a modular implantable medical device. Various functional components of a modular implantable medical device are separated into interconnected modules. This distributed architecture for the implantable medical device may permit the device footprint to be distributed over a larger area while making a profile of the device smaller. In addition, the multiple modules and the flexible interconnections between the modules may permit the overall shape of the implantable medical device to be formed to better match the body location into which it is to be implanted.

An overmold integrates the modules of a modular implantable medical device into a structure. In exemplary embodiments, the overmold is flexible, e.g., allows intermodule motion, and provides a biocompatible interface between the component modules and the patient. In some embodiments, the edge of the overmold forms a sloped interface that provides a slope from the top of the implantable medical device to a body surface, such as the cranium. The sloped interface may be defined by an angle, which may be greater than 90 degrees, and is preferably approximately equal to 135 degrees. The overmold may be preformed to a concave shape to better conform to a body surface, such as the cranium. The overmold may incorporate one or more motion reduction elements to restrict intermodule motion to certain directions or ranges in order to protect the structural integrity of interconnections between the modules.

The overmold can include elastomeric materials, such as silicone, and/or non-elastomeric materials such as polysulfone and polyurethane. Further, the overmold may include one or more components. For example, a first component may comprise an elastomeric material and at least partially encapsulates each of the modules, while a second component comprises a non-elastomeric material that surrounds, e.g., is located proximate to sides of one or more modules. The first component may provide biocompatibility, flexibility and a desired form factor for the modular implantable medical device. The second component may, for example, provide structural integrity for the modular implantable medical device, e.g., restrict intermodule motion, hold the one or more modules within the first component, and provide through-holes for secure attachment of the modular implantable medical device to a surface within the patient, such as the cranium.

In one embodiment, the invention is directed to an implantable medical device that includes a plurality of interconnected modules. Each of the modules comprises a housing. The implantable medical device further comprises an overmold that at least partially encapsulates each of the housings.

In another embodiment, the invention is directed to an implantable medical device comprising a housing and an overmold that at least partially encapsulates the housing. The overmold comprises a first component that at least partially encapsulates the housing and a second component that is located adjacent to side surfaces of the housing. The first component comprises an elastomeric material, and the second component comprises a non-elastomeric material.

In another embodiment, the invention is directed to an implantable medical device. The implantable medical device includes a plurality of interconnected modules, and each of the modules comprises a housing. The implantable medical device further comprises means for integrating the modules into a single structure that at least partially encapsulates each of the housings.

In another embodiment, the invention is directed to a method for fabricating a modular implantable medical device having an overmold. The method includes fabrication of an overmold, fabrication of a plurality of modules and interconnection members, fabrication of a motion reduction element, and combination of the overmold, motion reduction element and plurality of modules to construct the modular implantable medical device.

The details of one or more embodiments of the invention are set forth in the accompanying drawings and the description below. Other embodiments of the invention will be apparent from the description and drawings, and from the claims.

DETAILED DESCRIPTION

Figure 1A:
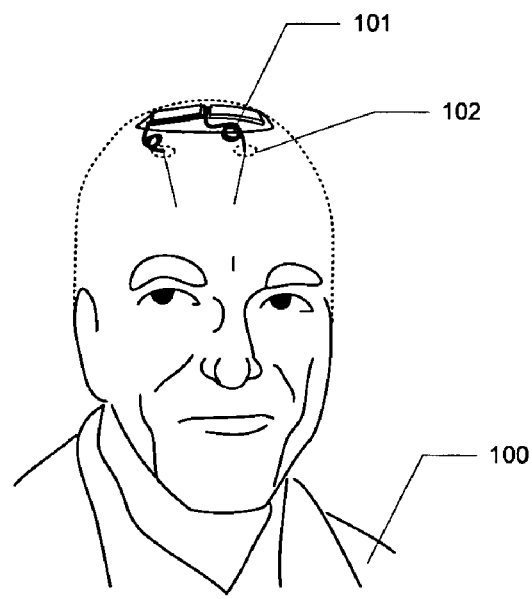
FIGS. 1A and 1B are conceptual diagrams illustrating a modular implantable medical device implanted in a patient according to an example embodiment of the present invention.
Figure 1B:
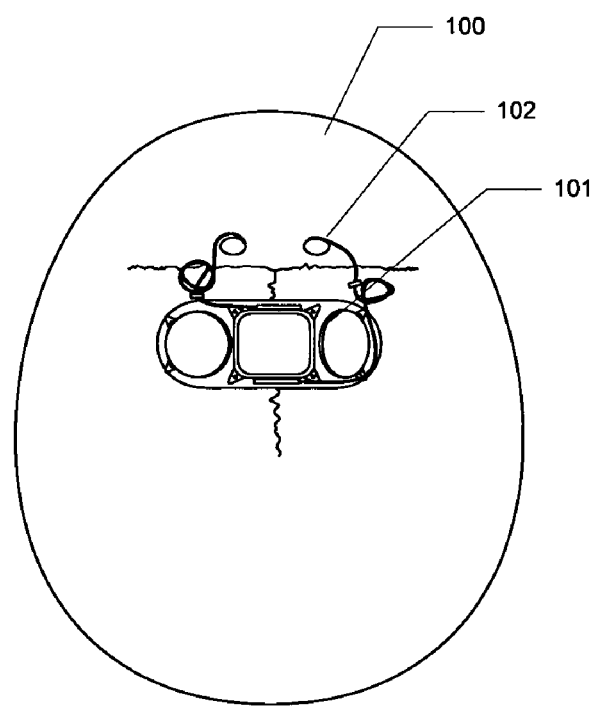

FIGS. 1A and 1B are conceptual diagrams illustrating a modular implantable medical device 101 implanted within a patient 100. By constructing modular implantable medical device 101 as a set of distributed modules connected together as described herein, modular implantable medical device 101 may be implanted at locations for which implantation of conventional implantable medical devices has been deemed undesirable, thus permitting the implantable medical device 101 to be implanted near a monitoring and/or therapy delivery location. In the example illustrated within FIGS. 1A–1B, modular implantable medical device 101 is implanted under the scalp of the patient 100 in order to locate the device 101 close to the location to which therapy is to be delivered via leads 102, i.e., the brain of patient 100. The low profile and the shape of modular implantable medical device 101 as described herein can reduce the risk of infection and skin erosion associated with implantation of matter beneath the scalp, and may provide a cosmetically acceptable profile when implanted beneath the scalp.

Modular implantable medical device 101 may deliver stimulation to the brain of patient 100 to, for example, provide deep brain stimulation (DBS) therapy, or to stimulate the cortex of the brain. Cortical stimulation may involve stimulation of the motor cortex. Modular implantable medical device 101 may be used to treat any nervous system disorder including, but not limited to, epilepsy, pain, psychological disorders including mood and anxiety disorders, movement disorders (MVD), such as, but not limited to, essential tremor, Parkinson's disease, and neurodegenerative disorders.

However, modular implantable medical device 101 is not limited to delivery of stimulation to the brain of patient 100, and may be employed with leads 102 deployed anywhere in the head or neck including, for example, leads deployed on or near the surface of the skull, leads deployed beneath the skull such as near or on the dura mater, leads placed adjacent cranial or other nerves in the neck or head, or leads placed directly on the surface of the brain. Moreover, modular implantable medical device 101 is not limited to implantation under the scalp of patient 100. Indeed, modular implantable medical device 101 may be implanted anywhere within patient 100. For example, modular implantable medical device 101 can be implanted within the neck of patient 100, and deliver stimulation to the vagus nerve or the cervical region of the spinal cord.

Modular implantable medical device 101 may alternatively be implanted within a pectoral region or the abdomen of patient 100 to act as a diaphragmatic pacer, or to provide any of the monitoring and therapy delivery functions known in the art to be associated with cardiac pacemakers. Further, modular implantable medical device 101 may be implanted in the upper buttock region and deliver spinal cord, urological or gastrological stimulation therapy, or may be configured to be implanted within the periphery, e.g., limbs, of patient 100 for delivery of stimulation to the muscles and/or peripheral nervous system of patient 100. As is the case with cranial implantation, the modularity of implantable medical device 101 may enable implantation at some of these example locations for which implantation of conventional implantable medical devices is generally deemed undesirable.

Modular implantable medical device 101 is not limited to embodiments that deliver stimulation. For example, in some embodiments modular implantable medical device 101 may additionally or alternatively monitor one or more physiological parameters and/or the activity of patient 100, and may include sensors for these purposes. Where a therapy is delivered, modular implantable medical device 101 may operate in an open loop mode (also referred to as non-responsive operation), or in a closed loop mode (also referred to as responsive). Modular implantable medical device 101 may also provide warnings based on the monitoring.

As discussed above, the ability of a modular implantable medical device 101 according to the invention to be implanted close to a region within patient 100 to be monitored enables the use of shorter leads 102. Shorter leads 102 may advantageously improve the accuracy of such sensors by reducing noise attributable to leads 102. Shorter leads 102 may also advantageously reduce the negative affects of imaging techniques such as magnetic resonance imaging "MRI" on a person implanted with implantable medical device 101.

Additional alternate embodiments for implantable medical devices implemented according to principles of the present invention may also include non-electrical based therapies such as targeted introduction of fluids and similar therapeutic materials using pumps and reservoirs of material. One skilled in the art will recognize that any number of implantable devices may be possible without deviating from the spirit and scope of the present invention as recited within the attached claims.

Figure 2:
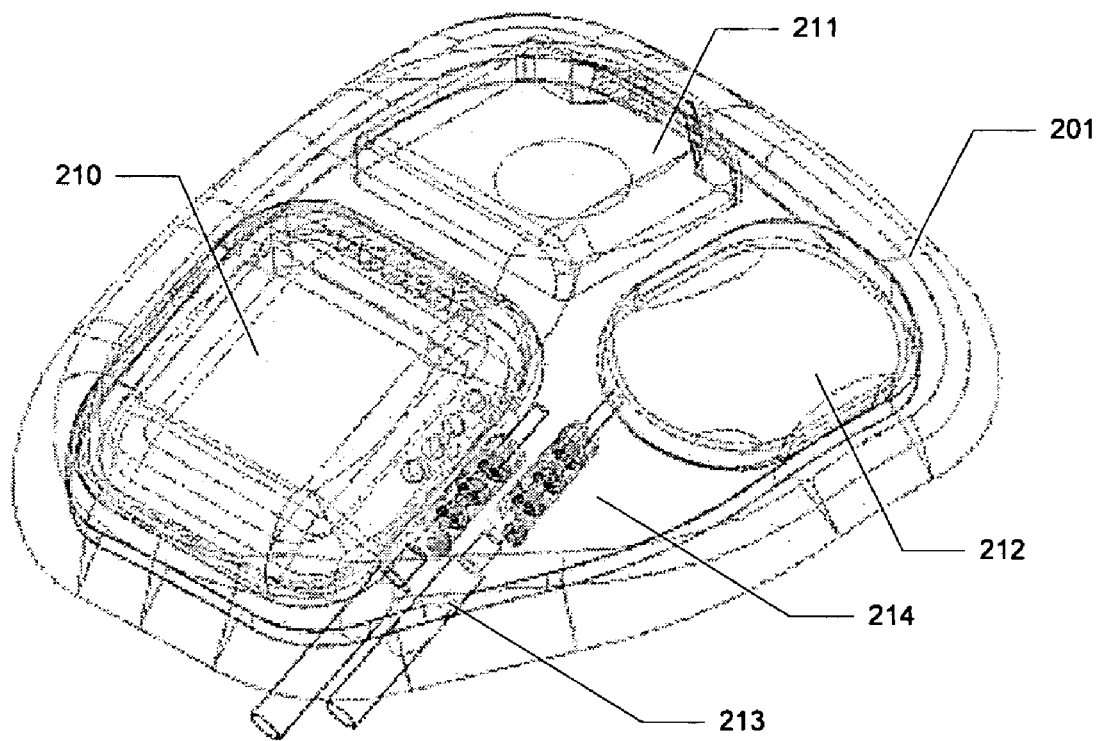
FIG. 2 is a schematic diagram illustrating a modular implantable medical device according to another embodiment of the present invention.

FIG. 2 is a schematic diagram illustrating a modular implantable medical device 201 according to another embodiment of the present invention. In this example embodiment, implantable medical device 201 is arranged in a triangular configuration. Modular implantable medical device 201 includes three modules: a control module 210, a power source module 211, and a recharge module 212. Each of modules 210–212 includes a respective housing. Modular implantable medical device 201 also contains a set of lead connection modules 213 that permits external leads 102 (FIGS. 1A and 1B) to be connected to control module 210 as needed. The distribution of functional components of modular implantable medical device 201 into modules permits modular implantable medical device 201 to possess a thin profile by spreading the components over a larger surface area.

Control module 210 includes control electronics for controlling the monitoring and/or therapy delivery functions of modular implantable medical device 201, such as a microprocessor, and may include therapy delivery circuitry. Power source module 211 includes a power source that provides energy to control module 210, which in some embodiments is a rechargeable power source such as a rechargeable battery and/or capacitor. Recharge module 212 includes a recharge coil for inductively receiving energy to recharge a rechargeable power source within power source module 211.

In some embodiments, one or modules may be coupled by coupling modules (not shown). A coupling module may be flexible, and may include a lumen to carry a conductor or a fluid between modules of a modular implantable medical device. In some embodiments, a coupling module is made of a flexible material such as silicone or a flexible polymer. In other embodiments a coupling module is hermetic and made of substantially less flexible material, such as titanium or stainless steel, and the flexibility of a coupling module is provided by the configuration and/or construction the coupling module.

A coupling module may be flexible in a plurality of directions to provide modules of a modular implantable medical device with multiple degrees of freedom of motion with respect to each other. In exemplary embodiments, a coupling module provides at least three degrees of motion, and the degrees of motion provided include rotational motion.

Additional details regarding modules 210, 211 and 212, additional or alternative modules for a modular implantable medical device, the interconnection of modules within a modular implantable medical device, and lead connection modules 213 may be found in commonly assigned U.S. patent application Ser. No. 10/731,869, entitled "MODULAR IMPLANTABLE MEDICAL DEVICE," commonly assigned U.S. patent application Ser. No. 10/731,699, entitled "COUPLING MODULE OF A MODULAR IMPLANTABLE MEDICAL DEVICE,"; and commonly assigned U.S. patent application Ser. No. 10/730,878, entitled "LEAD CONNECTIONMODULE OF A MODULAR IMPLANTABLE MEDICAL DEVICE,".

As illustrated in FIG. 2, modular implantable medical device 201 includes an overmold 214. Overmold 214 at least partially encapsulates modules 210–212. Further, as will be described in greater detail below, lead connection modules 213 may be formed in overmold 214. Overmold integrates modules 210–212 into a structure. Overmold 214 may provide a flexible structure that permits the device 501 to conform to a variety of implant locations.

In some embodiments, overmold 214 may be curved to match the shape of the location within a patient in which the device is being implanted. For example, implantation of modular implantable medical device 201 under the scalp of a patient may be accomplished if overmold 214 is concave to substantially conform to the shape of the cranium of the patient. Concavity of modular implantable medical devices is described in greater detail in a commonly-assigned U.S. patent application Ser. No. 10/731,867, entitled "CONCAVITY OF AN IMPLANTABLE MEDICAL DEVICE,". Any number of shapes may be used to match a particular implantable medical device 201 to an implantation location for a device.

Overmold 214 may comprise a solid biocompatible elastomeric material that is soft and flexible such as silicone. In some embodiments, overmold 214 comprises two or more materials, and two or more components. For example, overmold may comprise one or more elastomeric components formed of an elastomeric material, such as silicone, and one or more non-elastomeric components formed of a non-elastomeric material, such as polysulfone, or a polyurethane such as Tecothane®, which is commercially available from Hermedics Polymer Products, Wilmington, Mass. The one or more elastomeric components may provide the overall shape and flexibility of modular implantable medical device 201, while the non-elastomeric components may provide structural integrity for modular implantable medical device 201, restrict intermodule motion within modular implantable medical device 201 to certain ranges, and form a part of the lead interconnection modules 213. Further detail regarding reduction of intermodule motion within modular implantable medical devices may be found in a commonly-assigned U.S. patent application Ser. No. 10/731,881, entitled "REDUCING RELATIVE INTERMODULE MOTION IN A MODULAR IMPLANTABLE MEDICAL DEVICE".

FIGS. 3A–3F are schematic diagrams illustrating various arrangements of multiple modules within a modular implantable medical device 301 according to various embodiments of the present invention. In each of these embodiments, modular implantable medical device 301 has three modules as discussed above in reference to FIG. 2: a control module 210, a power source module 211, and a recharge module 212. These modules may be arranged into a variety of configurations, including those illustrated, as long as any required interconnections needed between the modules, e.g., coupling modules, may be routed within the device. The various embodiments include triangular configurations, in such as those shown in FIGS. 3A–C, and inline configurations, such as those shown in FIGS. 3D–F. The set of lead connection devices 313 may be located in various locations within the device as well.

Figure 3A:
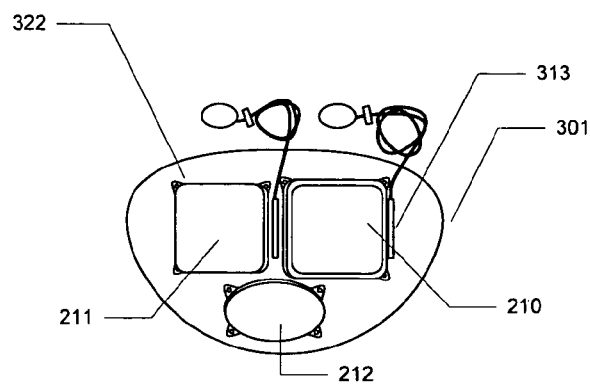
FIGS. 3A–3F are schematic diagrams illustrating various arrangements of modules within a modular implantable medical device according to various embodiments of the present invention.
Figure 3B:
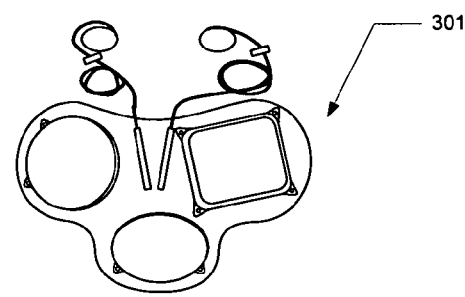
Figure 3C:
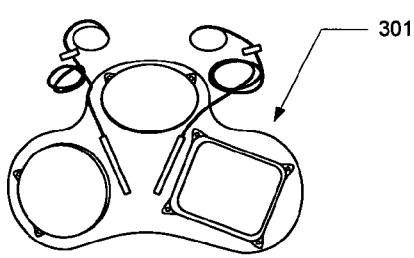
Figure 3D:
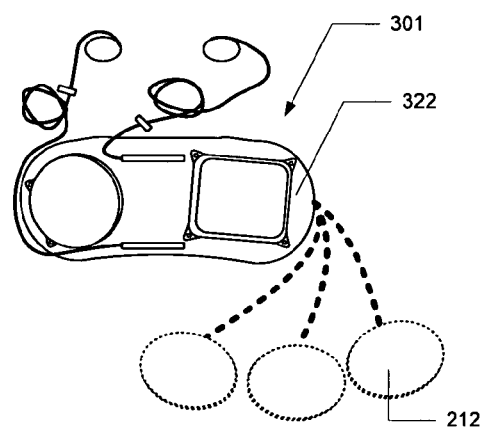
Figure 3E:
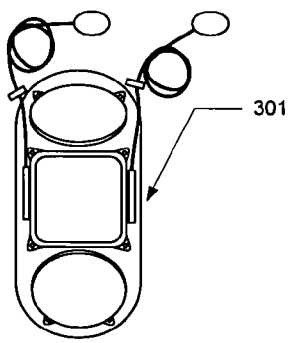
Figure 3F:
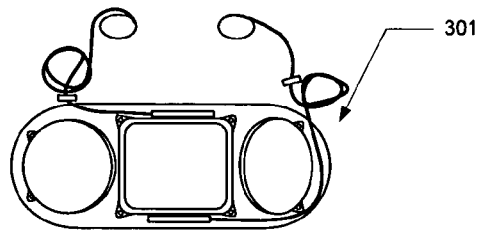

In some embodiments, such as those illustrated in FIGS. 3A–C and 3E–F, an overmold 322 at least partially encapsulates each of modules 210, 211 and 212. In other embodiments, such as that illustrated in FIG. 3D, at least one of the modules of modular IMD 301 is located outside of overmold 322. Module 212 located outside of overmold may, as shown in FIG. 3D, be tethered to overmold 322, allowing module 212 to be freely positioned some significant distance from overmold 322. Additional details relating to configurations of modules within a modular implantable medical devices and tethering of modules of an implantable medical device may be found in a U.S. patent application Ser. No. 10/731,869, entitled "MODULAR IMPLANTABLE MEDICAL DEVICE".

Figure 4A:
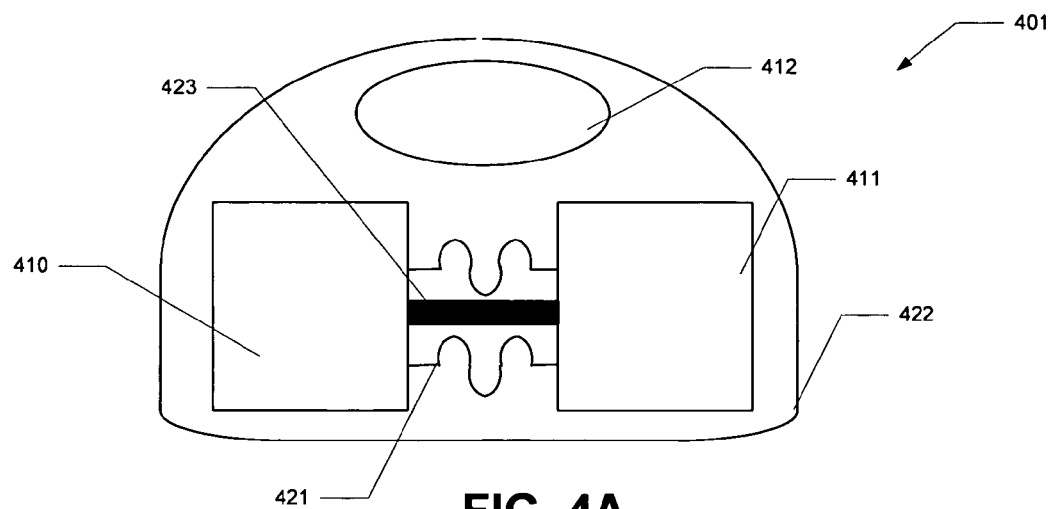
FIGS. 4A–4C are schematic diagrams illustrating the construction of an overmold of a modular implantable medical device according to the present invention.
Figure 4B:
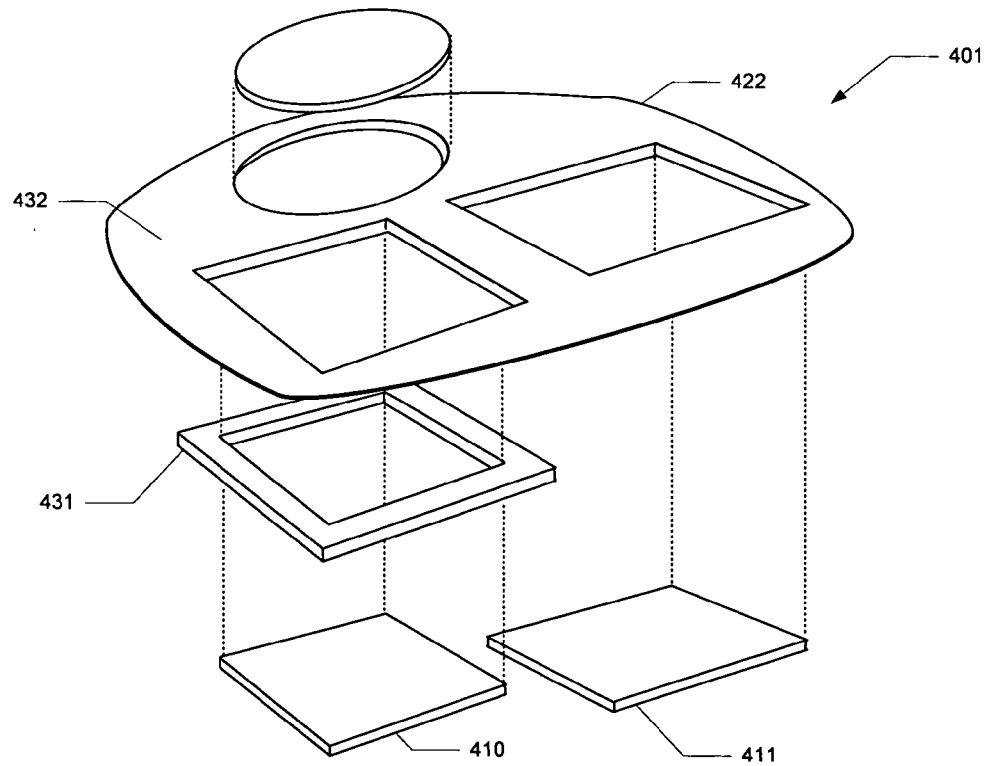
Figure 4C:
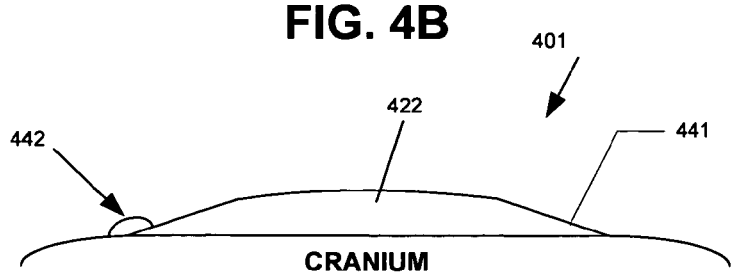

FIGS. 4A–4C are schematic diagrams illustrating an overmold 422 of a modular implantable medical device 401. FIG. 4A illustrates that the modular implantable medical device 401 comprises a set of modules 410–412, and a set of motion reduction elements 421 within overmold 422, such as motion reduction fibers connecting modules 410 and 411. Modules 410 and 411 are also coupled by a coupling module 423.

Because overmold 422 and coupling module 423 are flexible, overmold 422 and coupling module 423 may not provide sufficient motion reduction for the modules 410–412. Specifically, excessive relative motion between modules 410 and 411 may compromise the structural integrity of coupling module 424, which may lead to failure of modular implantable medical device 401. Motion reduction elements 421 are used to provide sufficient structural integrity to the device 401 once implanted into the patient 100 by restricting relative motion between modules 410 and 411 to certain directions or within certain ranges. Additional details regarding motion reduction elements 421 are described in co-pending and commonly assigned U.S. patent application Ser. No. 10/731,881, entitled "REDUCING RELATIVE INTER MODULE MOTION IN A MODULAR IMPLANTABLE MEDICAL DEVICE".

FIG. 4B illustrates that the overmold 422 may include two or more components, each component made of a different material. In particular, FIG. 4B illustrates the overmold 422 includes an elastomeric component 430 and a non-elastomeric component 431. The non-elastomeric component 431 is typically shaped to surround at least one of modules 410–412, i.e., is located proximate to sides of at least one of modules 410–412. In some embodiments, a plurality of individual non-elastomeric components 431 surround respective modules 410–412. In other embodiments, a non-elastomeric component 431 surrounds a plurality of modules 410–412 to integrate the surrounded modules in a common, semi-rigid structure.

The one or more non-elastomeric components 431 may be used to contain one or more modules within elastomeric component 430. Specifically, the one or more non-elastomeric components 431 may be formed to hold modules 410–412 within respective positions within elastomeric component 430. Elastomeric component 430 may, as shown in FIG. 4B, at least partially encapsulate each of modules 410–412 and provide an desired form factor for a modular implantable medical device. In some embodiments, non-elastomeric elements 431 are fitted into an elastomeric component 430 to form the overmold 422 before the electronic modules 410–412 are inserted into respective locations within overmold 422 where they will be contained by non-elastomeric elements 431.

Generally, overmold 422 provides a number of functions in including attaching to modules and other elements to provide a smooth interface surface for the device as it interacts with the patient, and protecting electrical connections and feed thru wires needed to connect modules to external leads.

Overmold 422 may be constructed from a durometric specific material to provide a clinically desirable device. In addition, a material used to construct the overmold 422 may possess a thermal conductivity characteristic to either act as a heat sink if needed to dissipate heat from modules 410–412, or a material to act as an insulator to shield the patient 100 from any excess heat from modules 410–412.

Because the implantable medical device 401 may be constructed from a large number of modules to perform a desired task, the materials selected for used in constructing the overmold 422 may vary as needed by each embodiment.

In embodiments in which overmold 422 is constructed of components 431 and 432, the device 401 may be fabricated by integrating components 431 and 432 to form the overmold 422, constructing the modules 410–412 and their respective connection modules 423, and constructing any motion reduction elements 421. Once all of these components are fabricated, the motion restriction elements 421 may be combined with the overmold 422, and the interconnected modules 410–412 may be inserted into the overmold 422 into respective positions where they are contained by components 431.

FIG. 4C illustrates that the overmold 422 provides sloped interface 441 between the modules within the device 401 and the patient's body components. In embodiments in which the device 401 is implanted within tight spaces, such as under the scalp, the sloped interface 441 provides a smooth transition between the body and the device modules 410–412. Protrusions are known to cause possible stress points for tissue that is located over implanted devices, which can, for example, lead to skin erosion in the case of a device implanted under the scalp. As such, the sloped interface 441 attempts to minimize the transition from the modules 410–412 and the edge of the device 401 to eliminate these points of stress. An angle of interface 442 from the patient's body and the sloped interface 441 is greater than 90 degrees. Angle 442 may be between 120 and 150 degrees, is preferably between 130 and 140 degrees, and is most preferably approximately 135 degrees.

Figure 5A:
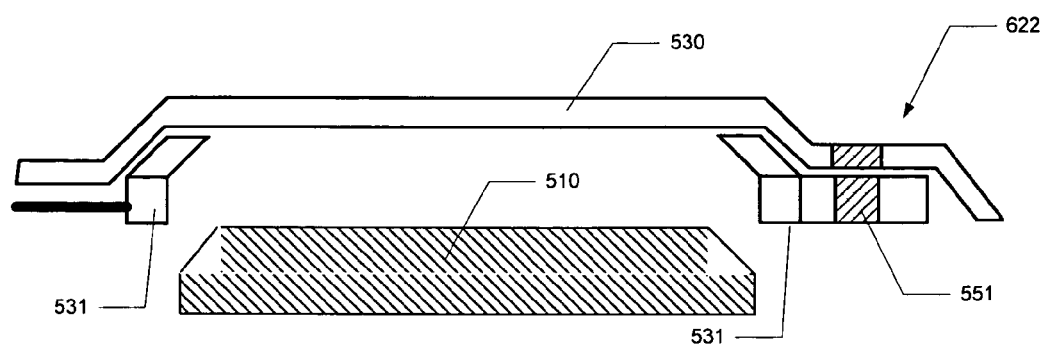
FIGS. 5A–5B are schematic diagrams illustrating the interaction of components of an overmold according to the present invention.
Figure 5B:
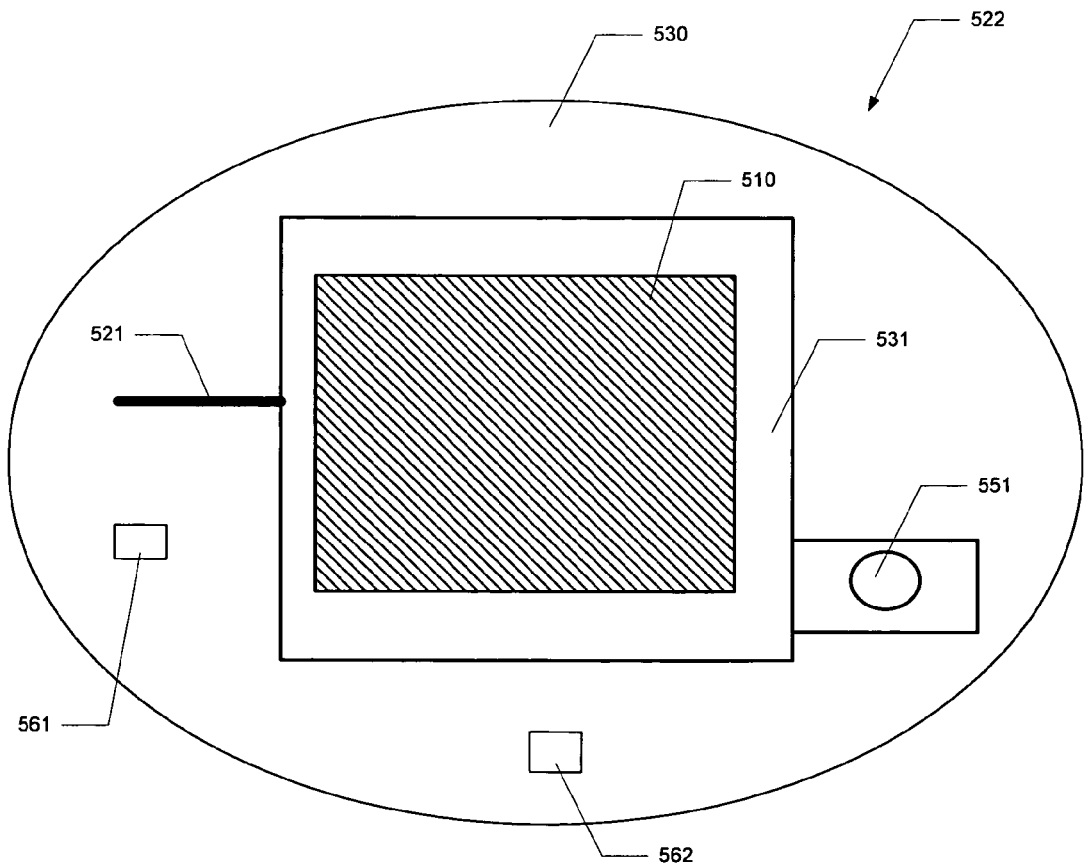

FIGS. 5A–5B are schematic diagrams illustrating the interaction of components of an implantable medical device that are part of an overmold. FIG. 5A provides a side cross-sectional view of an overmold 522 that includes an elestomeric component 530 and a non-elastomeric component 531 that interfaces with a control module 610. The non-elastomeric component 531 is shaped to mate with and surround the module 510, and may provide motion reduction for the module. Specifically, the non-elastomeric component 531 may be mechanically connected to at least one other module of a modular implantable medical device, e.g., to non-elastomeric components that surround other modules of an implantable medical device, by a motion reduction element 521. In other words, the overmold 522 encapsulates a plurality of modules in this embodiment, and each of the modules may be surrounded by a non-elastomeric component 531 that is connected to other non-elastomeric components by motion reduction elements 521.

A through hole 551 may be located through overmold 522, e.g., through elastomeric component 530 and non-elastomeric component 531, to provide an attachment point for the implantable medical device. In some embodiments, the implantable medical device may be secured in place using bone screws or similar attachment devices that secure the device to the patient. Such through holes 551 permit the device to be mechanically attached to the patient once the device is positioned at a desired location.

In addition, elastomeric component 530 is shown as completely encapsulating the modules and components within FIG. 5. However, in some embodiments, elastomeric component 530, like non-elastomeric component 531, may merely surround the module 510 but not cover the top of the module. Such an arrangement may render the profile of the overall device smaller. In such an alternate embodiment, a surface across the overmold and the electronics module 510 may minimize transition discontinuities to minimize profile changes that may interact with a patient after implantation. In other embodiments, one or both components 530 and 531 cover a top of module 510, or fully encapsulate module 510.

FIG. 5B illustrates a top view of the overmold 522 having an elastomeric component 530 that covers a non-elastomeric component 531 that surrounds the control module 510. The through hole 551 used as an attachment point is shown as part of the non-elastomeric component 531 that is covered by the elastomeric component 530. The shape of the non-elastomeric component 531 and control module 510 are shown as being rectangular in this embodiment. However, one skilled in the art will recognize that any shape for the non-elastomeric component 531 and control module 510 may be used without deviating from the spirit and scope of the present invention. Further, the shape of non-elastomeric component 531 need not be the same as that the shape of the component that it surrounds. The modules may be restrained within the overmold 522 using many restraint mechanisms known in the arts including attachment elements, adhesives, snap rings, and similar elements.

While the overmold 522 described above may be constructed from two different materials, a softer, more flexible elastomeric component 530 and one or more harder, more rigid non-elastomeric components 531, one skilled in the art may recognize that an overmold 522 may include a single component made of either class of material to provide the surface smoothing, module integration, and structural module restraint features described herein.

Finally, the overmold 522 may include several additional features unrelated to the above functions regarding the restraint and interconnection of multiple modules. In one embodiment, radio-opaque markers 561 and 562 may be imbedded within the overmold 522 to assist in determining an exact location of an implantable medical device within a patient. These radio-opaque markers 561 and 562 typically possess a non-symetrical shape to permit registration and orientation of the device 501 from imaging of the markers. These radio-opaque markers may be constructed using barium and similar materials that permit such imaging. A telemetry and/or recharge coil may be embedded directly within the overmold 522. Therapeutic agents, such as anti-infection and antiinflammatory agents may be impregnated within the overmold 522 to assist in complications that may arise from implantation and use of the implanted medical device.

Figure 6:
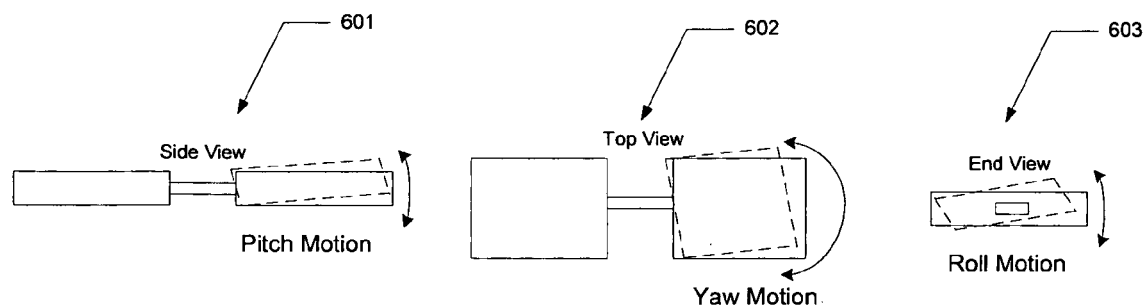
FIG. 6 is a schematic diagram illustrating the degrees of motion present in a modular implantable medical device.

FIG. 6 is a schematic diagram illustrating degrees of intermodular motion that may be present in modular implantable medical device. For any two modules within a distributed medical device, motion between the two modules may include pitch motion 601, yaw motion 602, and roll motion 603. For the motion reduction elements discussed above, one or more of these three degrees of motion may be limited to prevent mechanical failures of interconnections between the modules during use of a modular implantable medical device. Specifically, modules of a modular implantable medical device may be connected by connector modules, which may be compromised by excessive intermodule motion. Such interconnect members are described in greater detail in commonly assigned U.S. patent application Ser. No. 10/731,881, entitled "REDUCING RELATIVE INTERMODULE MOTION IN A MODULAR IMPLANTABLE MEDICAL DEVICE".

Figure 7:
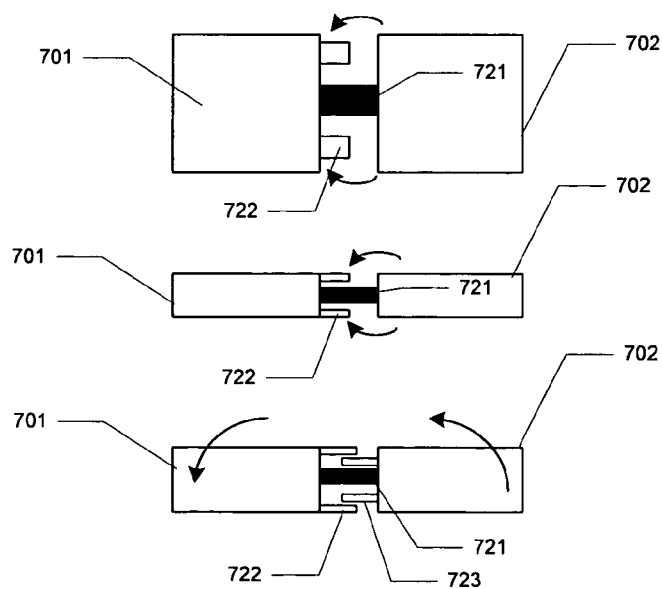
FIG. 7 is a schematic diagram illustrating motion reduction within various degrees of motion within a modular implantable medical device.

FIG. 7 is a schematic diagram illustrating motion reduction within various degrees of motion within a modular implantable medical device. For any two modules 701–702 within an implantable medical device, a connector module 721 may be used between the modules 701–702 to connect elements within these module 701–702. Motion reduction elements 722 and 723 may be used to reduce inter-modular motion, and in some cases, to limit inter-modular motion to a range of motion.

Motion reduction elements 722 and 723 may be formed as part of non-elastomeric components 531 of an overmold 522 associated with each of modules 701 and 702. As shown in FIG. 7, motion reduction elements 722 and 723 allow free inter-modular motion within one of the degrees within a range. In some embodiments, one non-elastomeric component includes one or more motion reduction elements 722. In other embodiments, two non-elastomeric components 531 include motion reduction elements 722 and 723, respectively, which interact to reduce inter-modular motion.

A modular implantable medical device may include any number of motion reduction elements, which may take any of a variety of shapes. In some embodiments, motion reduction elements may be used in all axes to maximize the amount of motion reduction provided. The implantable medical device having multiple modules typically requires sufficient motion reduction to prevent undue mechanical stresses on interconnection connection member 721 between the modules 701–702 that may not be provided by a flexible overmold 522.

Additional details regarding the set of motion reduction elements 521 are described in co-pending and commonly assigned U.S. patent application Ser. No. 10/731,881, entitled "REDUCING RELATIVE INTER MODULE MOTION IN A MODULAR IMPLANTABLE MEDICAL DEVICE".

Figure 8A:
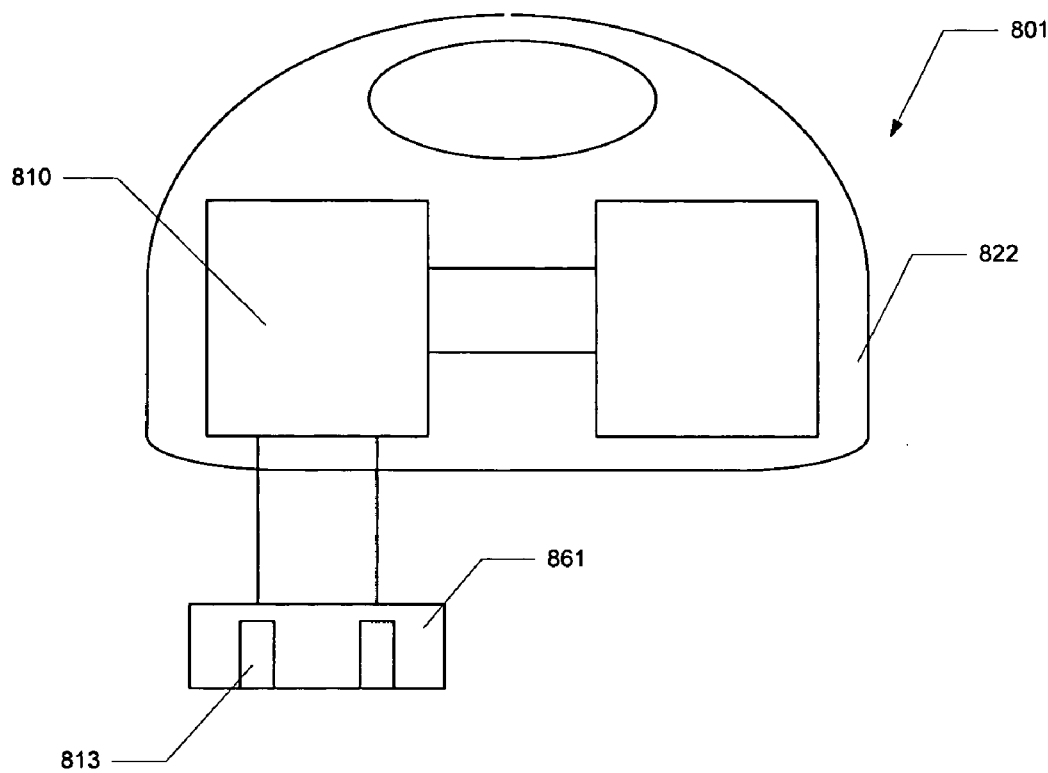
FIGS. 8A–C are schematic diagrams illustrating example embodiments of modular implantable medical devices having lead management features.

FIG. 8A is a block diagram illustrating an example embodiment of a modular implantable medical device 801 having a tethered lead interconnect site 861 according to the present invention. An overmold 822 of implantable medical device 801 at least partially encapsulates and connects a plurality of modules 810–812 while not encapsulating lead connection modules 813 that are part of tethered lead interconnect site 861. In such embodiments, the implantation of device 801 would not require the insertion of external leads into the overmold 822. In addition, the external leads may be located a distance away from the device 801. Such an arrangement may assist in the management of the external leads as they are placed within the patient and routed to a device implantation location. Further, location of leads and connection site 861 away from overmold 822 may make it less likely that the leads will be damaged during a surgical explant procedure.

Figure 8B:
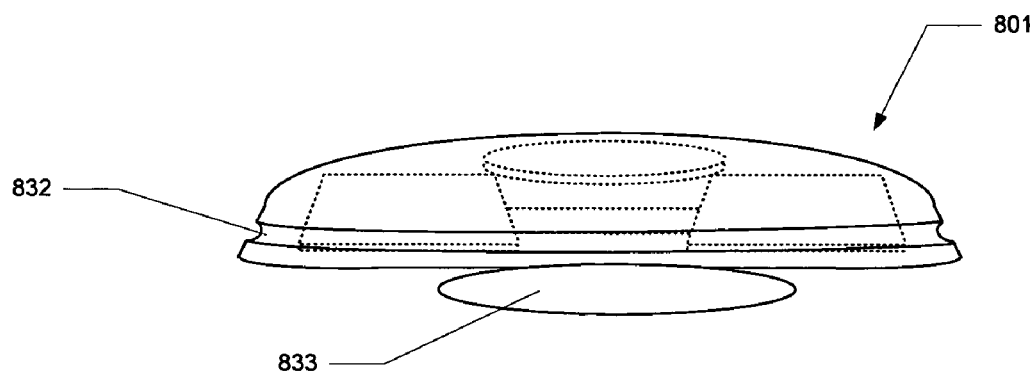
Figure 8C:
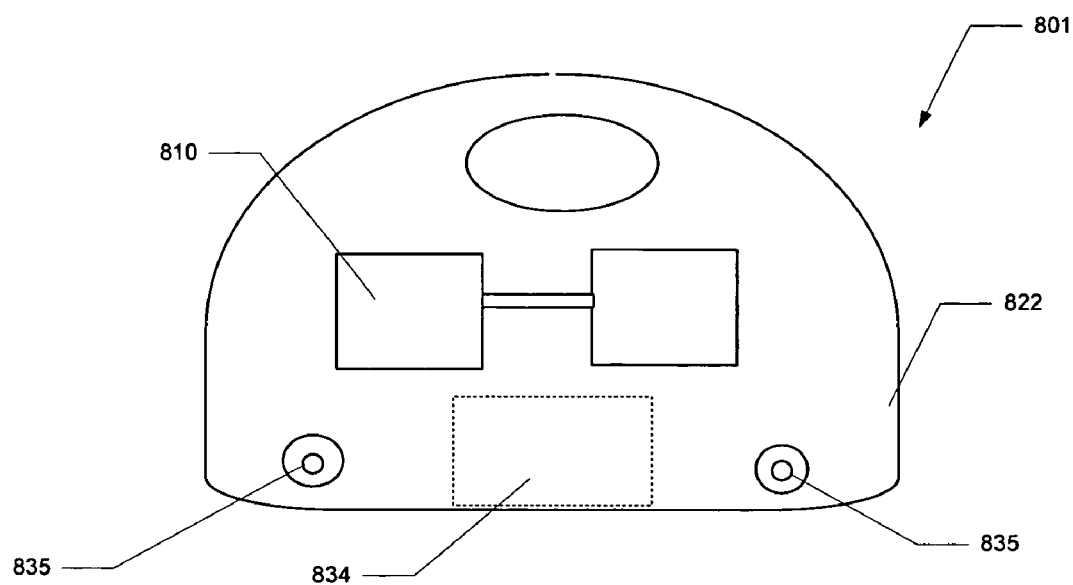

In alternate embodiments shown in FIGS. 8B–8C, overmold 822 may possess mechanical structures such as grooves 832, an externally attached pouch 833, or an integrated containment cavity 834 to contain and/or route the external leads away from the implantable medical device 801 in an efficient manner. In some embodiments, the external leads may possess a minimum length to provide a particular electrical characteristic for the implantable medical device 801. This minimum length may be greater than a distance needed by a particular patient for some implantation locations. These mechanical structures that assist in external lead management may accommodate any extra lead material that needs to be part of the device 801 in some implantation embodiments. Because the overmold may be spread over an area surrounding the modular device, the overmold may cover holes in the cranium formed to allow external leads to access the brain. Additional structures, including one or more cap structures 835 that secures a lead as it passes through the hole in the cranium may be an integral part of the overmold connector module 822.

Additional details regarding the lead connection modules described in co-pending and commonly assigned U.S. patent application Ser. No. 10/730,878, entitled "LEAD CONNECTION MODULE OF A MODULAR IMPLANTABLE MEDICAL DEVICE".

Figure 9:
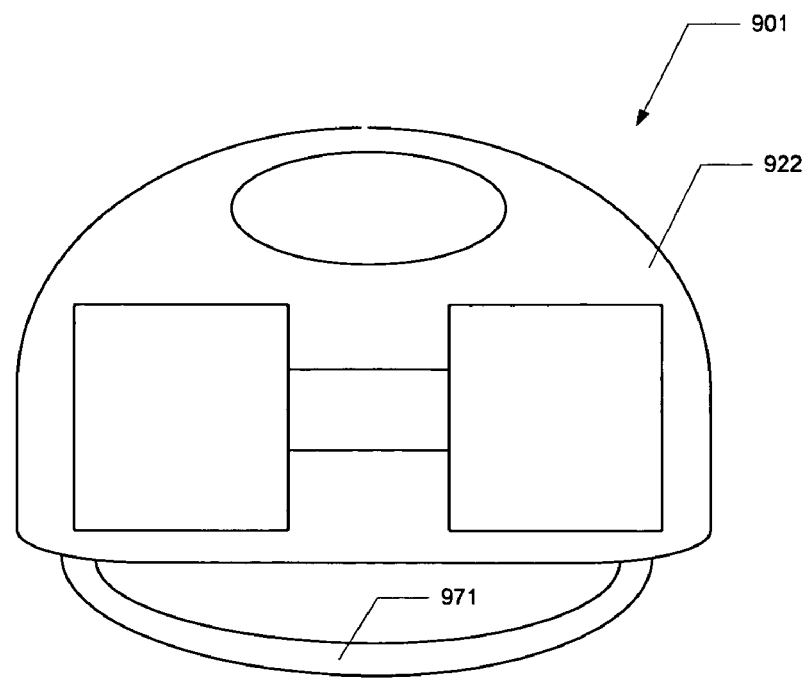
FIG. 9 is a schematic diagram illustrating an example embodiment of a modular implantable medical device having an access loop for removal.

FIG. 9 is a block diagram illustrating an example embodiment of a modular implantable medical device 901 having an access loop 971 for removal according to the present invention. Access loop 971 may be mechanically coupled to, or formed as a part of overmold connector module 922. This access loop 971 may be used to assist in the removal of the implantable medical device 901 at a point in time when the device 901 is no longer needed by the patient, or at a point in time when a particular device 901 needs to be replaced. The device 901 may be encapsulated within the patient 100 with scar tissue fibers such that physical effort will be required to remove the device 901 from its implantation location. This access loop 971 provides a clinician a removal assist structure to physically manipulate the implantable medical device 901 during its removal. This access loop 971 may also be useful during implantation of the device 901 as well as it provides a handle to manipulate the device 901 without handing the overmold 922 and its related modules. One skilled in the art will recognize that alternate embodiments for the access loop that may include removal handles, a strip cord and a reinforced opening within the overmold connector module to provide a mechanism to grasp the device to assist in removal.

Figure 10:
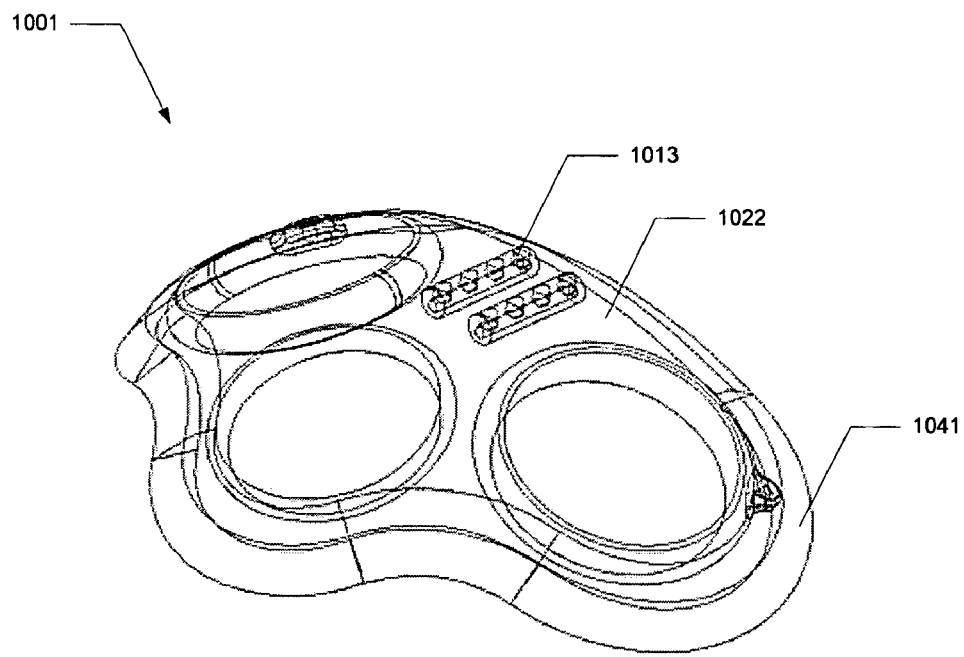
FIG. 10 is a schematic diagram illustrating a perspective view of an example embodiment of a modular implantable medical device having a triangular module arrangement.

FIG. 10 is a schematic diagram illustrating an example embodiment of a modular implantable medical device 1001 having a triangular module arrangement according to the present invention. In this embodiment, a triangular arrangement of modules is shown with a overmold 1022 that at least partially encapsulates all of the modules. Lead interconnection modules 1013 are located between the modules at a common location. Overmold 1022 provides a slope interface 1041.

Figure 11:
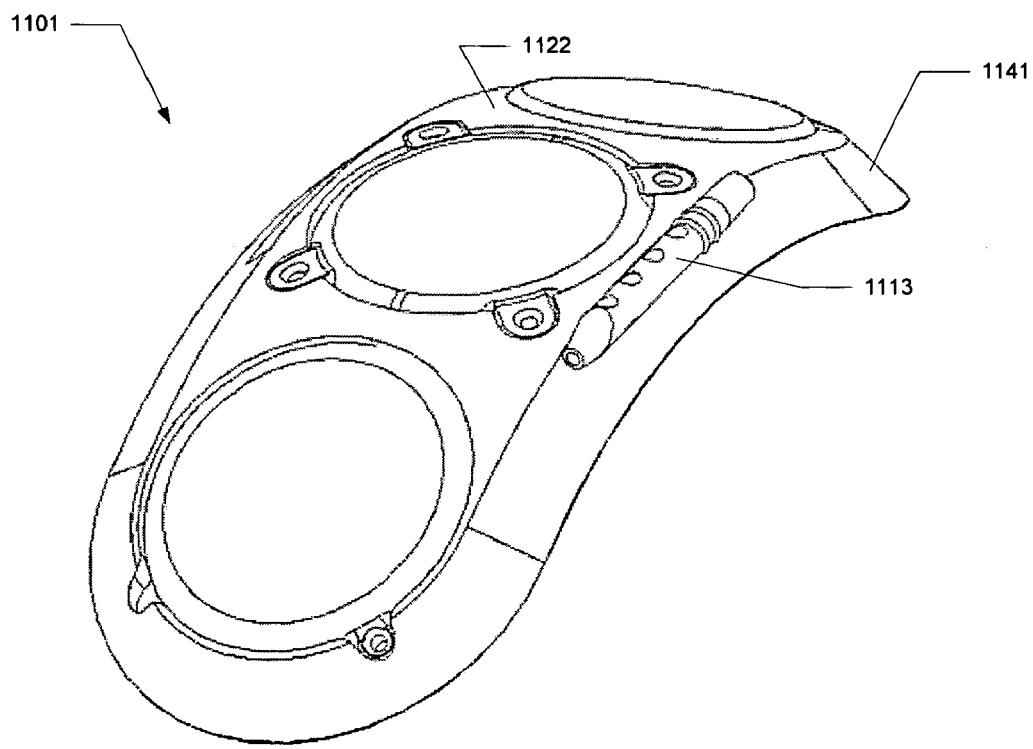
FIG. 11 is a schematic diagram illustrating a perspective view of an example embodiment of a modular implantable medical device having an inline module arrangement.

FIG. 11 is a schematic diagram illustrating an example embodiment of a modular implantable medical device 1101 having an inline module arrangement according to the present invention. In this embodiment, an inline arrangement of modules is shown with an overmold 1122 that at least partially encapsulates all of the modules. A lead interconnection module 1113 is located on one side of the overmold 1122. Overmold 1122 provides a slope interface 1141.

Figure 12:
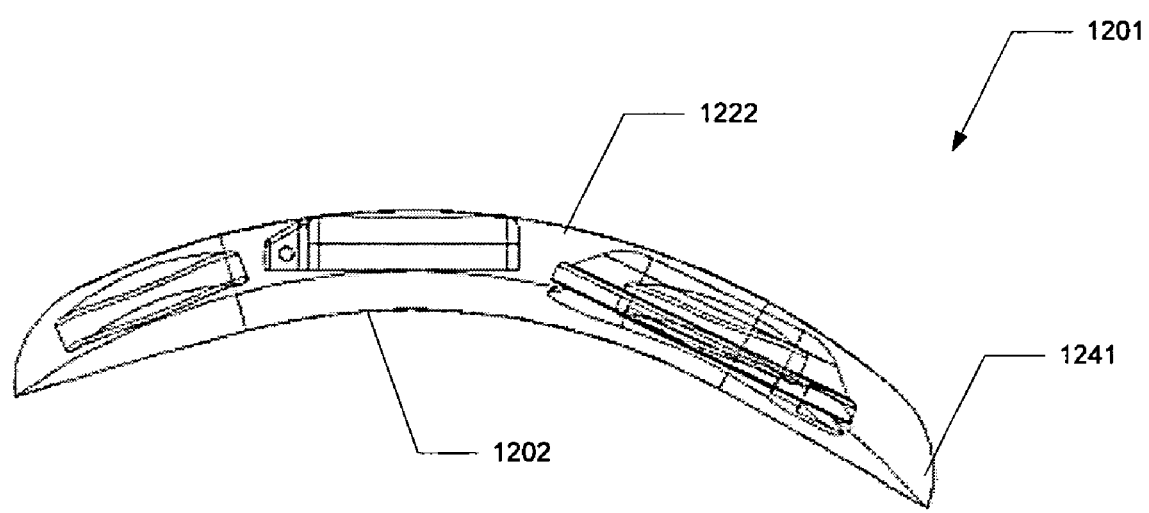
FIG. 12 is a schematic diagram illustrating side view of a modular implantable medical device having an inline module arrangement.

FIG. 12 is a schematic diagram illustrating side view of a multi-module implantable medical device having an inline module arrangement according to the present invention. The side view of the device 1201 shows an underside of the device 1202 that possess a curved shape to permit implantation at a location having a curved body structure.

Figure 13:
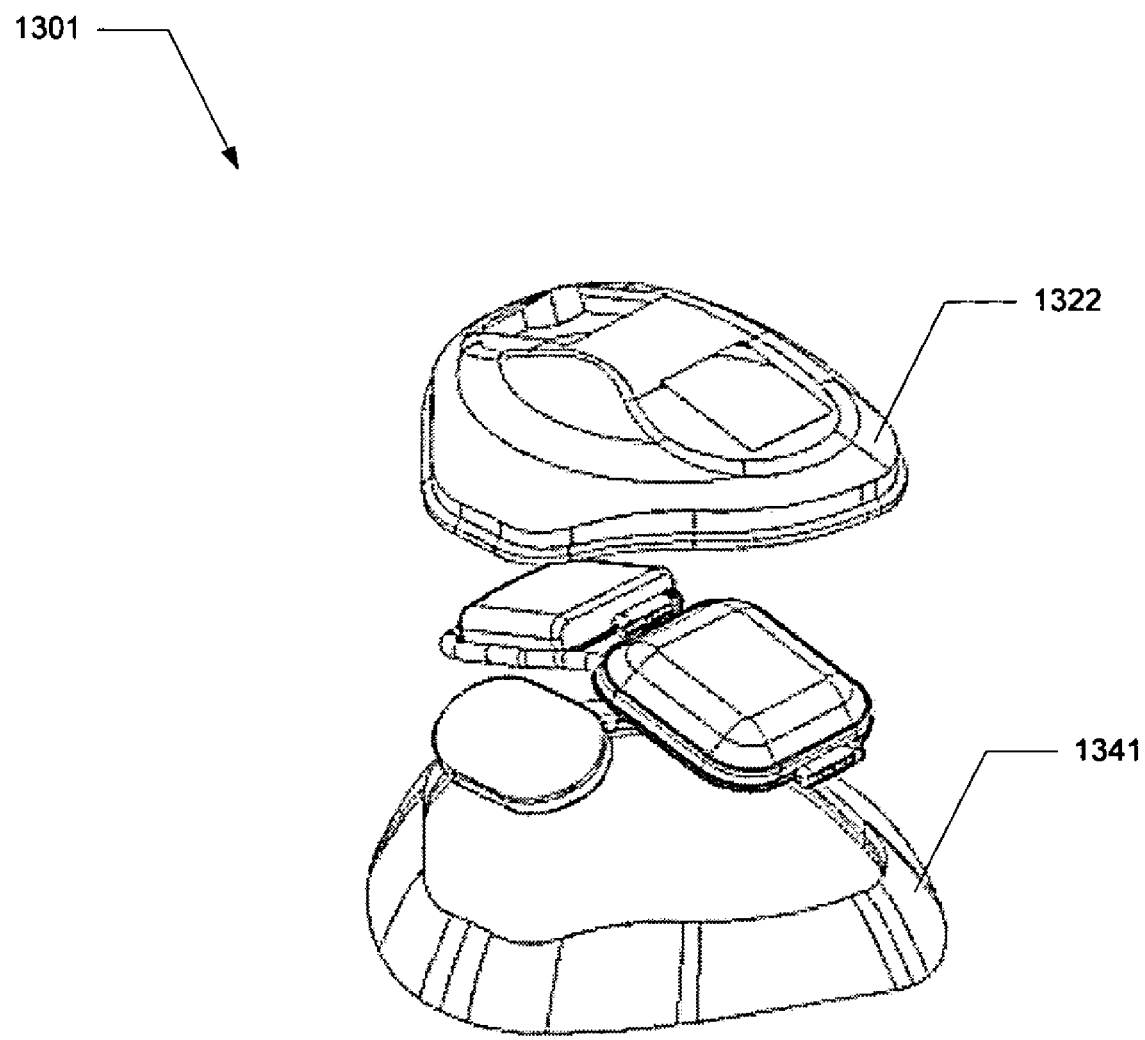
FIG. 13 is a schematic diagram illustrating an exploded view of a modular implantable medical device having a triangular module arrangement.

FIG. 13 is a schematic diagram illustrating an exploded view of a modular implantable medical device 1301 having a triangular module arrangement according to the present invention. In this embodiment, yet another triangular arrangement of modules is shown with an overmold 1322 at least partially encapsulating all of the modules. A slope interface element 1341 is shown surrounding the overmold 1322. In this embodiment, the slope interface element 1341 is shown as a separate physical structure, such as a flexible band, an o-ring, removable flexible flange, or a tapered outer contour element that surrounds the overmold 1322, rather than a tapered portion of overmold 1322. Slope interface element 1341 provides a desired sloped interface between the edge of the implantable medical device and the patient. In some embodiments, the shape and contour of slope interface element 1341 may be modified at the time of implantation to obtain a desired shape, or slope interface elements 1341 may be selected at the time of implantation from a variety of slope interface elements to provide a desired slope interface for a particular patient.

Figure 14:
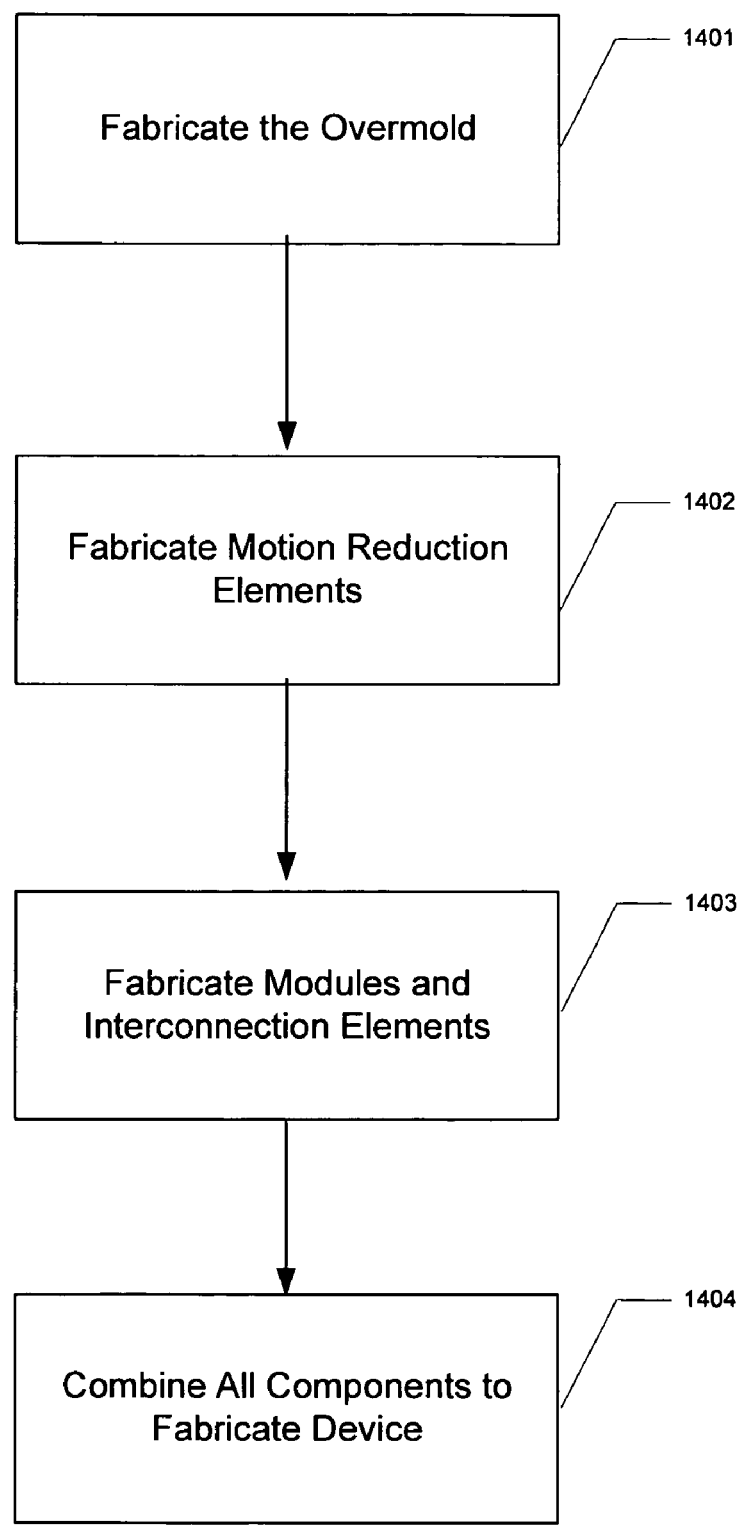
FIG. 14 is a flowchart illustrating a method of constructing an implantable medical device with an overmold according to the present invention.

FIG. 14 is a flowchart illustrating a method of constructing an implantable medical device with an overmold according to the present invention. An implantable medical device 401 may be fabricated by constructing the overmold 422 (1401) from a first and second component. As discussed above, overmold 422 may comprise two or more materials, and two or more components. For example, overmold may comprise one or more elastomeric components formed of an elastomeric material, such as silicone, and one or more non-elastomeric components formed of a non-elastomeric material. Once the overmold 422 is completed, the modules 410–412 with their respective connector modules 423 are constructed (1402). Next, any motion reduction elements 421 included in the device 401 are constructed. Once all of these components are fabricated, the motion restriction elements 421 may be combined with the overmold 422 (1403) and the interconnected modules 410–412 may be inserted (1404) into the overmold 422. From the combination of these components, the device 401 is formed.

While the above embodiments of the present invention describe a overmold for a modular implantable medical device, one skilled in the art will recognize that the invention is not so limited. For example, in some embodiments an implantable medical device comprises a single housing and an overmold that at least partially encapsulates the housing. It is to be understood that other embodiments may be utilized and operational changes may be made without departing from the scope of the present invention as recited in the attached claims.

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto.

The invention claimed is:

1. An implantable medical device comprising:
   a plurality of interconnected modules, each of the modules comprising a respective one of a plurality of housings; and
   an overmold that at least partially encapsulates each of the housings and includes a motion reduction element to reduce intermodule motion and provide structural integrity to the implantable medical device, the overmold being at least partially flexible, wherein the overmold comprises a first component that at least partially encapsulates each of the housings and a second component that is positioned to surround at least one of the housings, and
   wherein a portion of the implantable medical device is tapered to provide a sloped transition between an edge of the implantable medical device and a surface of a patient, and an angle between the edge of the implantable medical device and the surface of the patient is greater than 90 degrees.

2. The implantable medical device of claim 1, wherein the overmold comprises an elastomeric material.

3. The implantable medical device of claim 2, wherein the elastomeric material is silicone.

4. The implantable medical device of claim 1, wherein the overmold comprises a non-elastomeric material.

5. The implantable medical device of claim 4, wherein the non-elastomeric material is one of a polysulfone and a polyurethane.

6. The implantable medical device of claim 1, wherein the first component comprises an elastomeric material, arid the second component comprises a non-elastomeric material.

7. The implantable medical device of claim 1, further comprising a lead connection module within the overmold for connecting an external lead to electronics within one of the plurality of interconnected modules.

8. The implantable medical device of claim 1, wherein the overmold comprises a first overmold, the implantable medical device further comprising a second overmold that at least partially encapsulates a lead connection module, wherein the second overmold is tethered to the first overmold.

9. The implantable medical device of claim 1, wherein an edge of the overmold is tapered to provide the sloped transition between the implantable medical device and the surface of the patient, and an angle between the edge of the overmold and the surface of the patient is greater than 90 degrees.

10. The implantable medical device of claim 9, wherein the angle is within a range from 120 to 150 degrees.

11. The implantable medical device of claim 10, wherein the angle is approximately equal to 135 degrees.

12. The implantable medical device of claim 1, further comprising a sloped interface element, separate from the overmold, that surrounds the overmold and provides a sloped transition between the implantable medical device and the surface of the patient, wherein an angle between an edge of the sloped interface element and the surface of the patient is greater than 90 degrees.

13. The implantable medical device of claim 12, wherein the angle is within a range from 120 to 150 degrees.

14. The implantable medical device of claim 13, wherein the angle is approximately equal to 135 degrees.

15. The implantable medical device of claim 12, wherein the sloped interface element comprises at least one of a flexible band, an o-ring, a removable flexible flange, or a tapered outer contour element.

16. The implantable medical device of claim 1, wherein the overmold is concave to conform substantially to a cranium of a patient.

17. The implantable medical device of claim 1, wherein the overmold is molded prior to implantation to conform substantially to a cranium of a patient.

18. The implantable medical device of claim 1, wherein the overmold includes durometer specific material.

19. The implantable medical device of claim 1, wherein the overmold comprises a material having a high thermal conductivity to act as a heat sink for thermal energy generated within the modules.

20. The implantable medical device of claim 1, wherein the overmold comprises a material having a low thermal conductivity to act as a shield of thermal energy generated within the modules.

21. The implantable medical device of claim 1, wherein the overmold includes an external lead management structure for external leads being routed away from the implantable medical device.

22. The implantable medical device of claim 21, wherein the overmold includes a groove to hold external lead material.

23. The implantable medical device of claim 21, wherein the overmold includes a pouch to hold external lead material.

24. The implantable medical device of claim 1, wherein the overmold includes a removal assist structure for assisting in removal of the implantable medical device.

25. The implantable medical device of claim 1, wherein the overmold includes a through-hole to receive an attachment mechanism for attaching the implantable medical device to a patient.

26. The implantable medical device of claim 1, further comprising a radio-opaque marker within the overmold.

27. The implantable medical device of claim 1, wherein the overmold is impregnated with a therapeutic agent.

28. The implantable medical device of claim 1, wherein the implantable medical device is adapted to be implanted on a cranium of a patient, and the overmold includes a cap to cover a hole through the cranium.

29. The implantable medical device of claim 1, wherein at least one of the modules provides neurostimulation therapy to a patient.

30. The implantable medical device of claim 1, wherein the surface of the patient is the cranium.

31. An implantable medical device comprising:
a plurality of modules with respective housings; and
an overmold that at least partially encapsulates each of the housings and includes a motion reduction element to reduce intermodule motion, wherein the overmold comprises a first component that at least partially encapsulates each of the housings and a second component that is positioned to surround at least one of the housings, wherein the first component comprises an elastomeric material, and the second component comprises a non-elastomeric material.

32. The implantable medical device of claim 31, wherein the overmold is flexible.

33. The implantable medical device of claim 31, wherein the elastomeric material is silicone, and the non-elastomeric material is one of a polysulfone and a polyurethane.

34. The implantable medical device of claim 31, wherein the second component includes the motion reduction element.

35. The implantable medical device of claim 31, further comprising a lead connection module formed within the overmold for connecting an external lead to electronics the housing.

36. The implantable medical device of claim 35, wherein the second component forms at least a part of the lead connection module.

37. The implantable medical device of claim 31, wherein an edge of the first component is tapered to provide a sloped interface with a surface of a patient, and an angle between the edge and the surface of the patient is greater than 90 degrees.

38. The implantable medical device of claim 37, wherein the angle is within a range from 120 to 150 degrees.

39. The implantable medical device of claim 38, wherein the angle is approximately equal to 135 degrees.

40. The implantable medical device of claim 37, wherein the surface of the patient is the cranium.

41. The implantable medical device of claim 31, further comprising a sloped interface element that surrounds the overmold and provides a sloped interface with a surface of a patient, and an angle between an edge of the sloped interface element and the surface of the patient is greater than 90 degrees.

42. The implantable medical device of claim 41, wherein the surface of the patient is the cranium.

43. The implantable medical device of claim 31, wherein at least one of the first and second components of the overmold is concave such that the overmold conforms substantially to a cranium of a patient.

44. The implantable medical device of claim 31, wherein the second component includes a through-hole to receive an attachment mechanism for attaching the implantable medical device to a patient.

45. The implantable medical device of claim 31, wherein implantable medical device provides neurostimulation therapy to a patient.

46. An implantable medical device, comprising:
a plurality of interconnected modules, each of the modules comprising a respective one of a plurality of housings;
means for integrating the modules into a single structure, the means for integrating at least partially encapsulating each of the housings, wherein the means for integrating is at least partially flexible and comprises means for reducing intermodule motion; and
a sloped interface element, separate from the means for integrating, that surrounds the means for integrating and is tapered to provide a sloped transition between an edge of the means for integrating and a surface of a patient, wherein an angle between an edge of the sloped interface element and the surface of the patient is greater than 90 degrees.

47. The implantable medical device of claim 46, wherein the means for integrating comprises a means for providing flexibility for the implantable medical device and a means for providing structural integrity for the implantable medical device.

48. The implantable medical device of claim 46, wherein the means for integrating comprises means for connecting an external lead to electronics within one of the plurality of interconnected modules.

49. The implantable medical device of claim 46, wherein the means for integrating comprises means for holding external lead material.

50. The implantable medical device of claim 46, wherein the means for integrating comprises means for facilitating removal of the implantable medical device.

51. The implantable medical device of claim 46, wherein the means for integrating comprises means for receiving an attachment mechanism for attaching the implantable medical device to a patient.

52. The implantable medical device of claim 46, wherein the surface of the patient is the cranium.

53. A method for fabricating a modular implantable medical device, the method comprising:
fabricating a plurality of modules, each of the modules comprising a respective one of a plurality of housings;
fabricating a non-elastomeric component to surround at least one of the housings;
fabricating an elastomeric component to at least partially encapsulate each of the housings and the non-elastomeric component;
fabricating a motion reduction element to be positioned within the elastomeric component and reduce intermodule motion; and combining the elastomeric component non-elastomeric component, motion reduction element and plurality of modules to construct the modular implantable medical device.

54. The method according to claim 53, wherein the elastomeric component provides an overall shape and flexibility of modular implantable medical device.

55. The method according to claim 53, wherein the non-elastomeric component provides structural integrity for modular implantable medical device.

\* \* \* \* \*